United States Patent
Knapp

(10) Patent No.: US 9,295,811 B2
(45) Date of Patent: *Mar. 29, 2016

(54) URETERAL ACCESS SHEATH

(71) Applicant: C. R. Bard, Inc., Murray Hill, NJ (US)

(72) Inventor: Tracey E. Knapp, Lawrenceville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,353

(22) Filed: Dec. 12, 2014

(65) Prior Publication Data
US 2015/0099930 A1    Apr. 9, 2015

Related U.S. Application Data

(63) Continuation of application No. 14/094,611, filed on Dec. 2, 2013, now Pat. No. 8,911,415, which is a continuation of application No. 10/840,882, filed on May 7, 2004, now Pat. No. 8,597,261, which is a continuation-in-part of application No. 10/409,527, filed on Apr. 8, 2003, now Pat. No. 7,654,989.

(51) Int. Cl.
*A61M 25/01*     (2006.01)
*A61B 1/307*     (2006.01)
(Continued)

(52) U.S. Cl.
CPC .............. *A61M 25/01* (2013.01); *A61B 1/307* (2013.01); *A61B 1/32* (2013.01); *A61M 25/0032* (2013.01); *A61M 25/0097* (2013.01); *A61M 25/0662* (2013.01); *A61M 2025/0037* (2013.01); *A61M 2025/0177* (2013.01)

(58) Field of Classification Search
CPC ............. A61M 25/01; A61M 2025/0037; A61M 25/0662; A61M 2025/0177; A61M 25/0032; A61M 25/0097; A61B 1/32; A61B 1/307
USPC .................................... 600/104; 604/264, 43
See application file for complete search history.

(56) References Cited

U.S. PATENT DOCUMENTS

| | | |
|---|---|---|
| 2,235,979 A | 3/1941 | Brown |
| 2,286,462 A | 6/1942 | Chaffin |

(Continued)

FOREIGN PATENT DOCUMENTS

| | | |
|---|---|---|
| EP | 0515119 A1 | 11/1992 |
| JP | 6511409 T | 12/1994 |

(Continued)

OTHER PUBLICATIONS

AquaGuide Ureteral Access Sheath, "Kink Resistance: Comparison of the AquaGuide Ureteral Access Sheath Compared to Competitive Access Sheaths," C. R. Bard, Inc. (2003).

(Continued)

*Primary Examiner* — Manuel Mendez
(74) *Attorney, Agent, or Firm* — Rutan & Tucker, LLP

(57) ABSTRACT

In one embodiment, an access sheath includes a sheath assembly including sheath tubing, the sheath tubing having a main lumen and a secondary lumen that extends along the length of the main lumen. The main lumen has a first cross-sectional area, a first length, and a distal end outlet. The secondary lumen has a second cross-sectional area less than the first cross-sectional area, a second length less than the first length, and a distal end outlet terminating proximal of the main lumen distal outlet.

13 Claims, 19 Drawing Sheets

(51) Int. Cl.
*A61B 1/32* (2006.01)
*A61M 25/00* (2006.01)
*A61M 25/06* (2006.01)

(56) References Cited

U.S. PATENT DOCUMENTS

| | | | |
|---|---|---|---|
| 2,911,968 | A | 11/1959 | Phillips |
| 4,557,255 | A | 12/1985 | Goodman |
| 4,741,326 | A | 5/1988 | Sidall et al. |
| 4,750,488 | A | 6/1988 | Wuchinich et al. |
| 4,798,193 | A | 1/1989 | Giesy et al. |
| 4,802,461 | A | 2/1989 | Cho |
| 4,834,702 | A | 5/1989 | Rocco |
| 4,899,733 | A | 2/1990 | DeCastro et al. |
| 5,078,701 | A | 1/1992 | Grassi et al. |
| 5,127,393 | A | 7/1992 | McFarlin et al. |
| 5,195,958 | A | 3/1993 | Phillips |
| 5,199,417 | A | 4/1993 | Muller et al. |
| 5,292,311 | A | 3/1994 | Cope |
| 5,324,306 | A | 6/1994 | Makower et al. |
| 5,342,383 | A | 8/1994 | Thomas |
| 5,370,617 | A | 12/1994 | Sahota |
| 5,391,155 | A | 2/1995 | Sachse |
| 5,397,302 | A | 3/1995 | Weaver et al. |
| 5,483,951 | A | 1/1996 | Frassica et al. |
| 5,569,215 | A | 10/1996 | Crocker |
| 5,571,093 | A | 11/1996 | Cruz et al. |
| 6,395,021 | B1 | 5/2002 | Hart et al. |
| 6,440,123 | B1 | 8/2002 | Engel |
| 6,470,219 | B1 | 10/2002 | Edwards et al. |
| 6,488,662 | B2 | 12/2002 | Sirimanne |
| 6,811,542 | B2 | 11/2004 | Liska et al. |
| 7,150,737 | B2 | 12/2006 | Purdy et al. |
| 7,654,989 | B2 | 2/2010 | Knapp |
| 8,597,261 | B2 * | 12/2013 | Knapp .................. 604/284 |
| 2001/0027295 | A1 | 10/2001 | Dulak et al. |
| 2002/0038115 | A1 | 3/2002 | Dulak et al. |
| 2002/0188175 | A1 | 12/2002 | Levine et al. |
| 2003/0114732 | A1 | 6/2003 | Webler et al. |
| 2014/0088518 | A1 | 3/2014 | Knapp |

FOREIGN PATENT DOCUMENTS

| | | | |
|---|---|---|---|
| WO | 0066212 | A1 | 11/2000 |
| WO | 0074760 | A2 | 12/2000 |

OTHER PUBLICATIONS

AquaGuide Ureteral Access Sheath, partial product brochure, Bard Endourology, (undated, describing products of 2001, 2002, and 2003) (27 sheets, 2 pages per sheet).
AquaGuide Ureteral Access Sheath, The Original Multi-Tasker, Product Manual, Bard (2003).
Bard 10 French Dual Lumen Ureteral Catheter, Bard Urological Division, 1999.
EP 04759272.0 filed Apr. 8, 2004 Office Action dated Oct. 15, 2010.
Introducing the NExt Generation of Ureteral Access Sheaths from Cook, Flexor Ureteral Access Sheath, Product Brochure, Cook, 2002.
JP Application 2006-509810 filed Apr. 8, 2004 Office Action dated Jul. 6, 2010.
JP Application 2006-509810 filed Apr. 8, 2004 Office Action dated Nov. 10, 2009.
PCT/US2004/010821 filed Apr. 8, 2004 International Preliminary Report on Patentability dated Jul. 24, 2006.
PCT/US2004/010821 filed Apr. 8, 2004 Search Report dated Sep. 8, 2004.
PCT/US2004/010821 filed Apr. 8, 2004 Written Opinion dated Sep. 8, 2004.
U.S. Appl. No. 10/409,527, filed Apr. 8, 2003 Non-Final Office Action dated Mar. 4, 2009.
U.S. Appl. No. 10/409,527, filed Apr. 8, 2003 Notice of Allowance dated Dec. 8, 2009.
U.S. Appl. No. 10/840,882, filed May 5, 2004 Ex Parte Quayle Action dated May 20, 2013.
U.S. Appl. No. 10/840,882, filed May 5, 2004 Final Office Action dated Jun. 10, 2009.
U.S. Appl. No. 10/840,882, filed May 5, 2004 Final Office Action dated Oct. 5, 2010.
U.S. Appl. No. 10/840,882, filed May 5, 2004 Non-Final Office Action dated Jul. 24, 2008.
U.S. Appl. No. 10/840,882, filed May 5, 2004 Non-Final Office Action dated Oct. 28, 2009.
U.S. Appl. No. 10/840,882, filed May 5, 2004 Notice of Allowance dated Aug. 2, 2013.
U.S. Appl. No. 14/094,611, filed Dec. 2, 2013 Non-Final Office Action dated May 9, 2014.

* cited by examiner

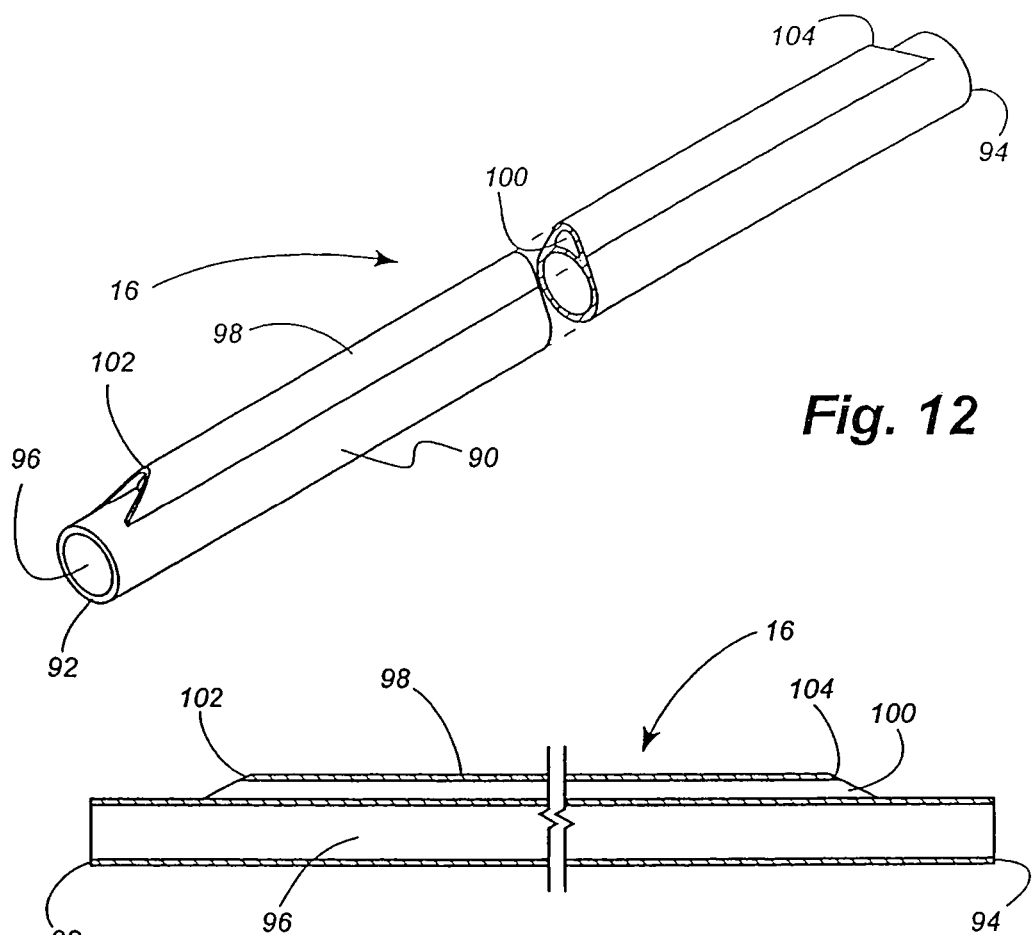
*Fig. 12*
*Fig. 13*
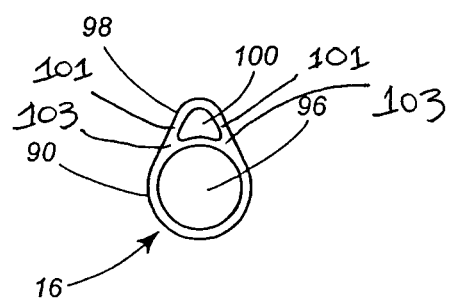
*Fig. 14*

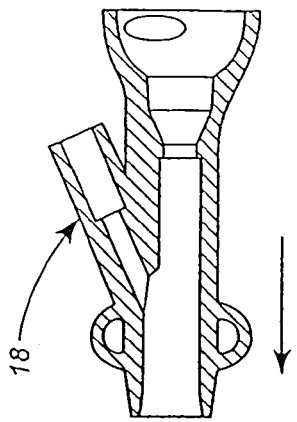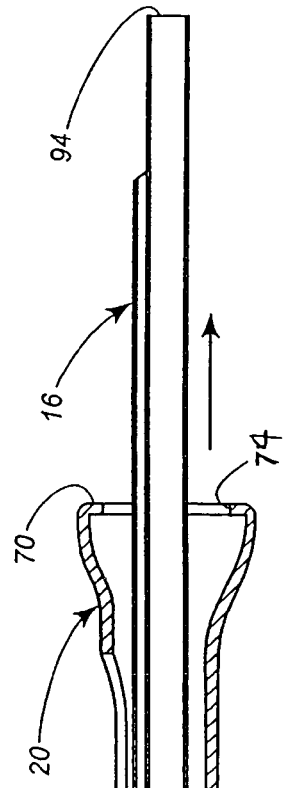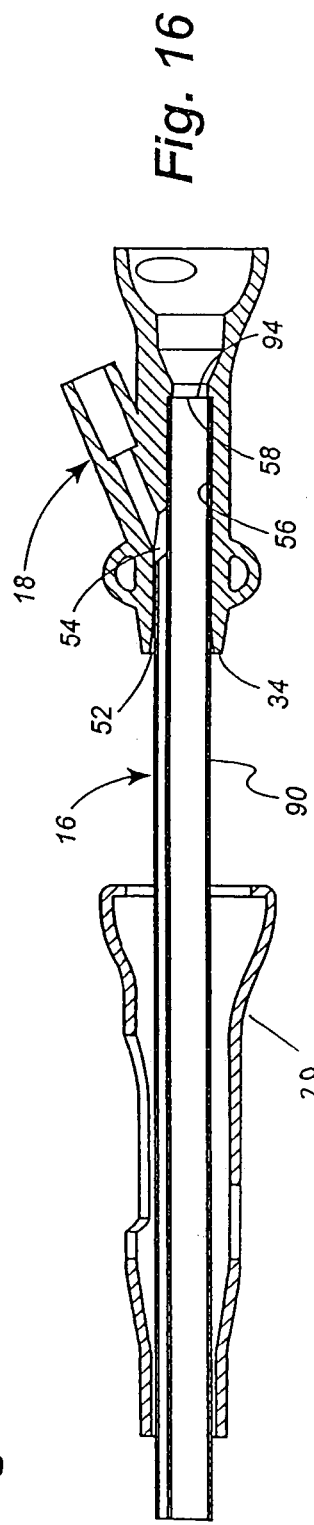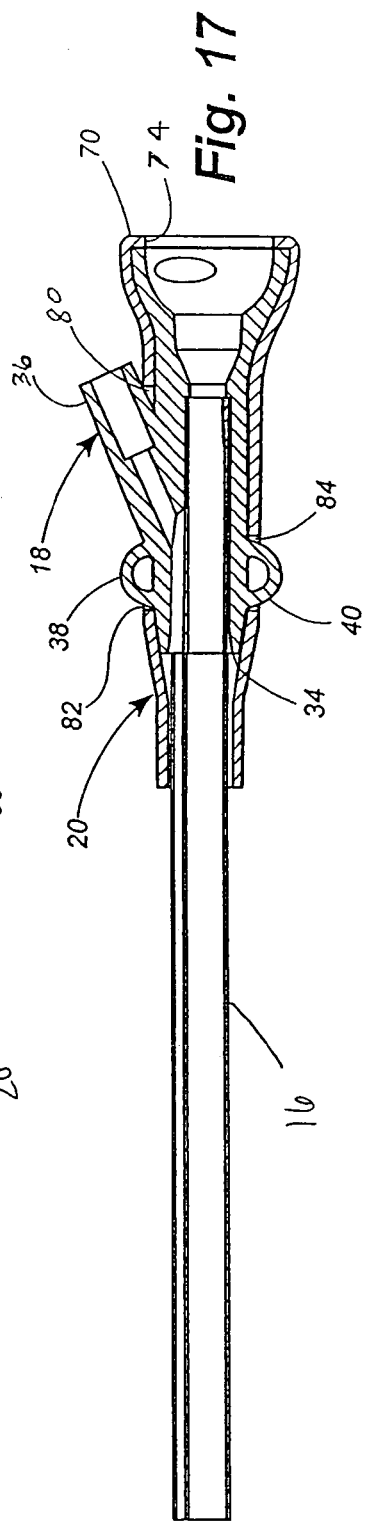

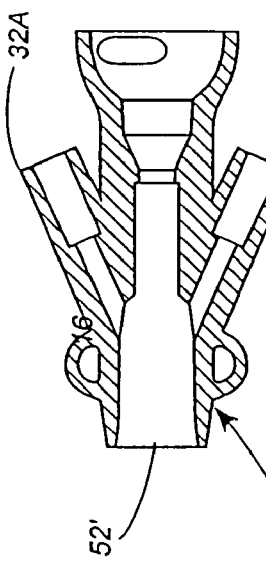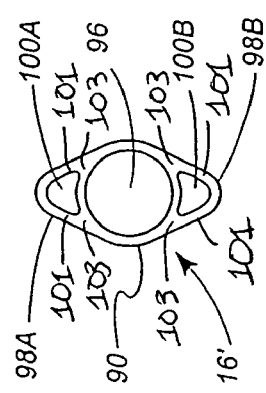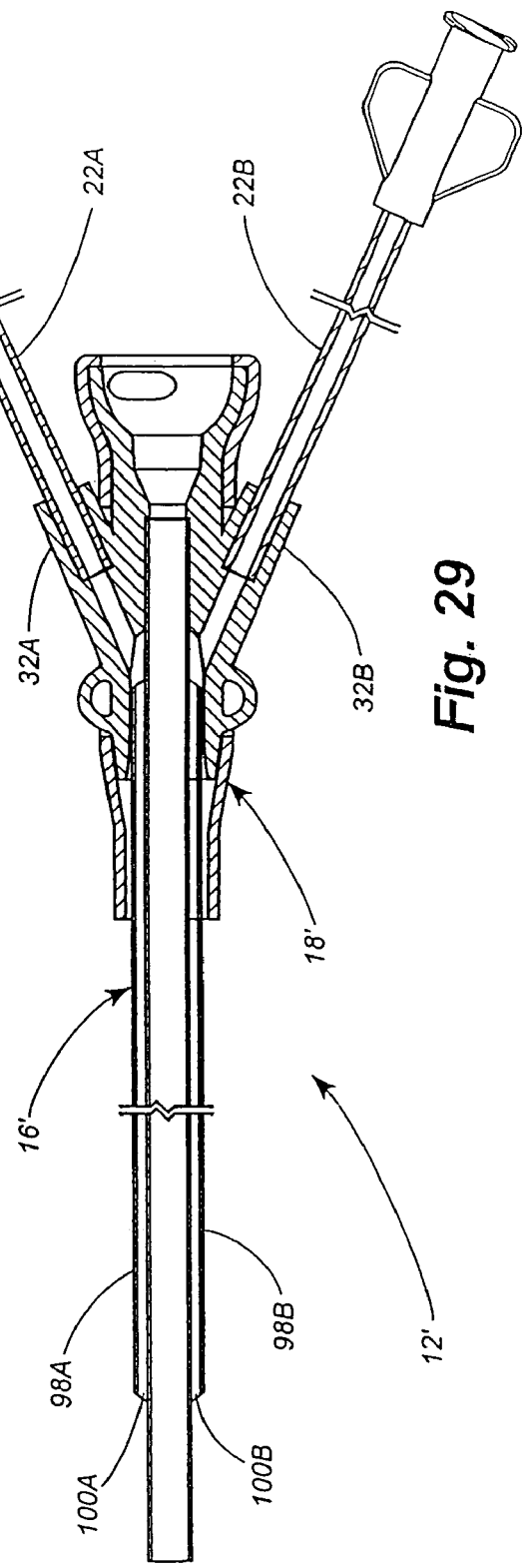
Fig. 28
Fig. 27
Fig. 29

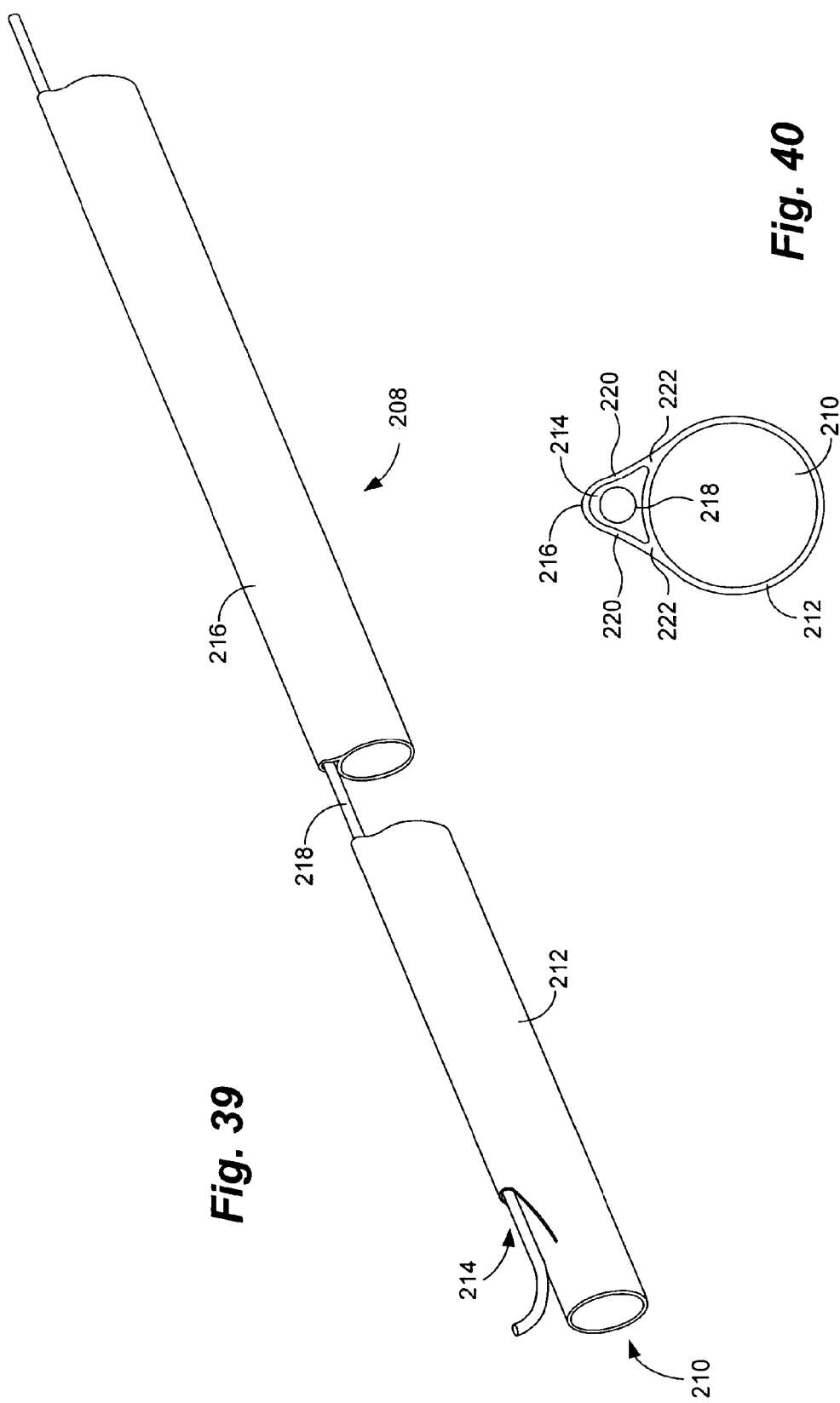

URETERAL ACCESS SHEATH

CROSS-REFERENCE TO RELATED APPLICATIONS

This application is a continuation of U.S. patent application Ser. No. 14/094,611, filed Dec. 2, 2013, now U.S. Pat. No. 8,911,415, which is a continuation of U.S. patent application Ser. No. 10/840,882, filed May 7, 2004, now U.S. Pat. No. 8,597,261, which is a continuation-in-part of U.S. patent application Ser. No. 10/409,527, filed Apr. 8, 2003, now U.S. Pat. No. 7,654,989, each of which is entirely incorporated herein by reference.

BACKGROUND

It is known to use a ureteral access sheath for creating an access channel from the external meatus to a location within the ureter of a patient to perform surgical procedures within the ureter and/or kidney. With an established channel to the ureter, a surgeon is able to insert and to withdraw a ureteroscope or other instrument more rapidly and with limited trauma to a patient's urinary system.

A typical prior art ureteral access sheath includes two subassemblies: a dilator and a sheath. The dilator is placed within the sheath, and the dilator and sheath combination is advanced through the urethra, through the bladder, and to the ureter. The dilator is then withdrawn, leaving the sheath in place. A ureteroscope is then advanced through the sheath to access the ureter.

A problem with known prior art ureteroscopic procedures concerns the need to irrigate the target site. Irrigation is critical during most ureteroscopic procedures. Since the inability to view the surgical area could have devastating effects, a procedure will not be continued until adequate viewing is achieved. Typically, irrigation fluid is supplied through the working channel of the ureteroscope. Because other instruments (i.e., a stone basket, grasper, laser fiber, etc.) also occupy the working channel, the flow rate of the irrigation fluid is reduced in proportion to the diameter of the instrument being used. Thus it would be desirable to provide a surgical environment in which the flow rate of irrigation fluid is not restricted by the presence of instruments within the working channel of the ureteroscope.

An additional problem with known prior art ureteral access sheaths concerns the need for guidewires in conjunction with the placement of the sheath. To use a typical prior art ureteral access sheath, the physician performs the following steps:

1. A cystoscope is inserted into the patient's urethra and advanced into the bladder, where the ureteral orifices are identified.
2. Using the cystoscope, a guidewire is inserted into the ureteral orifice.
3. Using fluoroscopy, the proximal end of the guidewire is inserted through the ureter and into the kidney.
4. With the guidewire carefully held in place, the cystoscope is removed over the guidewire.
5. The dilator is placed within the sheath.
6. The distal end of the ureteral access sheath is now back-loaded onto the proximal end of the guidewire and advanced over the guidewire and into the ureter. Advancement and position of the ureteral access sheath is usually verified with fluoroscopy.
7. The dilator is removed from the sheath.

Now the sheath is in place to provide a working channel from outside the patient to the ureter. However, on occasion a surgical procedure may inadvertently puncture or lacerate the ureter. Normally, a secondary "safety wire" has been placed for access, in the event the access sheath needs to be adjusted or otherwise removed. The safety wire is normally placed alongside the sheath. Placement of the secondary safety wire requires a number of additional steps:

8. The safety wire is inserted into the lumen of the sheath and advanced into the kidney.
9. With both the original guidewire and the safety wire held in place, the sheath is removed.
10. The dilator is placed into the sheath.
11. The sheath is back-loaded onto the initial guidewire as explained before and advanced into the ureter.
12. The dilator is removed from the sheath.

At this juncture, the sheath is in place, the original guidewire is disposed within the sheath, and the safety wire runs along the outside of the sheath. However, because the original guidewire occupies the same channel of the sheath into which the ureteroscope will be inserted, the original guidewire must now be removed before a surgical procedure can be commenced. Hence, 13. The guidewire is removed from the sheath.

As can be seen, the requirement for a safety wire located outside the working channel of the sheath adds a number of steps and additional time and complexity to the procedure of positioning the sheath. In addition, the presence of the safety wire within the ureter alongside the sheath increases the possibility of lacerating the ureter.

In addition, some surgical procedures require the removal from the ureter of objects that are larger than the lumen of the sheath. In such instances, the objects are grasped against the distal end of the sheath, and the sheath must be completely withdrawn from the patient to extract the object. The sheath may be repositioned by once again placing the dilator into the sheath and advancing the sheath over the safety wire. However, there is now no safety wire running alongside the sheath. To position another safety wire alongside the sheath, the sequence of steps previously set forth must be repeated.

Thus there is a need for a ureteral access sheath which minimizes the number of steps required to position the sheath.

There is a further need for an improved ureteral access sheath which facilitates the placement of a safety wire.

SUMMARY

In one embodiment, an access sheath includes a sheath assembly including sheath tubing, the sheath tubing having a main lumen and a secondary lumen that extends along the length of the main lumen, the main lumen being large enough to receive an endoscope.

BRIEF DESCRIPTION OF THE DRAWINGS

The disclosed ureteral access sheath will now be described with reference to the following drawings. Objects in the drawings are not necessarily drawn to scale.

FIG. 12 is an isometric view of the sheath tubing of the ureteral access sheath of FIG. 1.

FIG. 13 is a side cutaway view of the sheath tubing of FIG. 12.

FIG. 14 is an end view of the sheath tubing of FIG. 12.

FIG. 15 is a side cutaway view illustrating the assembly of the sheath tubing of FIG. 12 through the elastomeric cover of FIG. 6 and into the hub of FIG. 2.

FIG. 16 is a side cutaway view of the hub of FIG. 2 mounted onto the end of the sheath tubing of FIG. 12.

FIG. 17 is a side cutaway view of the assembly of FIG. 16 with the elastomeric cover of FIG. 6 fitted over the hub of FIG. 2.

FIG. 27 is an end view of a sheath tubing for use with the hub of FIG. 28.

FIG. 28 is a side cutaway view of a hub of an alternative embodiment of a ureteral access sheath.

FIG. 29 is a side cutaway view of an alternative embodiment of a ureteral access sheath comprising the hub of FIG. 28 and the sheath tubing of FIG. 27.

FIG. 39 is a partial, cutaway view of a further ureteral access sheath shown with a guidewire extending through a secondary lumen of the sheath.

FIG. 40 is an end view of the sheath and guidewire shown in FIG. 39.

DETAILED DESCRIPTION

Figure 1:
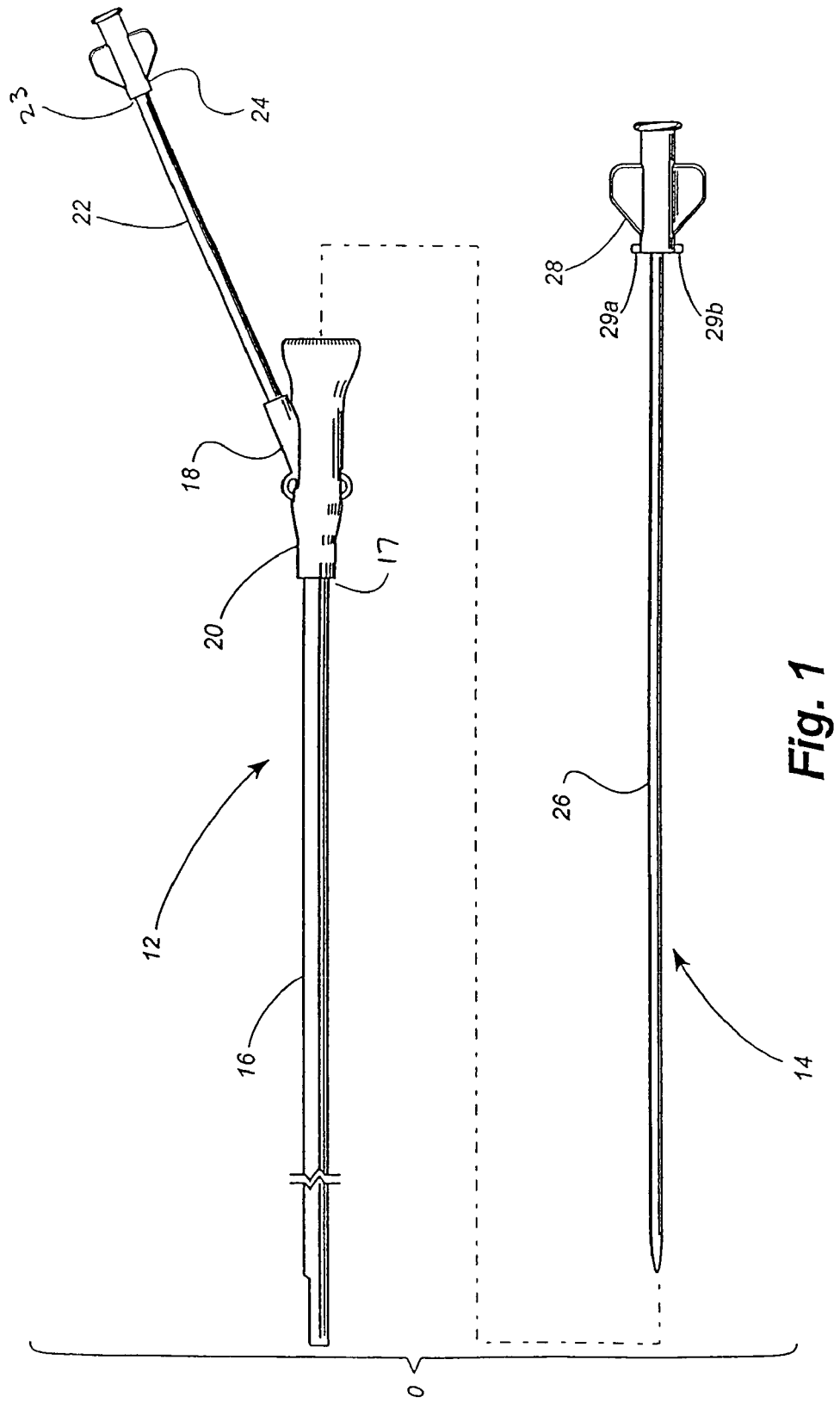
FIG. 1 is an exploded view of a ureteral access sheath according to a first disclosed embodiment.

Referring now to the drawings, in which like numerals indicate like elements throughout the several views, FIG. 1 depicts a ureteral access sheath according to a first embodiment. The ureteral access sheath 10 comprises a sheath assembly 12 and a dilator assembly 14, which fits within the sheath assembly 12 when the ureteral access sheath 10 is being positioned within a patient.

The sheath assembly 12 includes an elongated sheath tubing 16 having a distal end 17 and a proximal end coupled to a hub 18. The hub 18 is partially encased within an elastomeric cover 20. A leader tube 22 is also coupled to the hub 18. A female luer fitting 24 is mounted to the proximal end 23 of the leader tube 22.

The dilator assembly 14 comprises a dilator tubing 26 having a dilator luer 28 attached to the proximal end of the tubing. A pair of locking tabs 29a, b are formed or otherwise provided at a distal portion of the luer 28.

FIG. 1 is intended to provide only a general overview of the ureteral access sheath 10. Each of the components of the sheath assembly 12 will be more fully described with respect to additional drawing figures.

Figure 2:
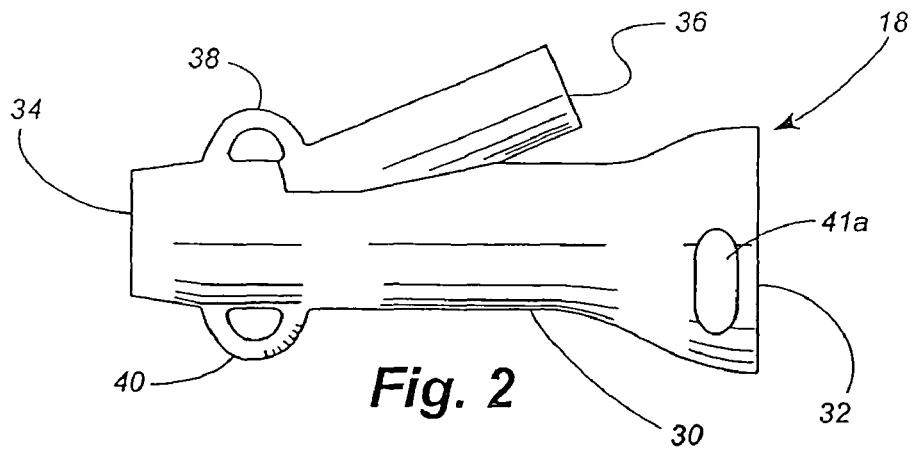
FIG. 2 is a side view of a hub of the ureteral access sheath of FIG. 1.

Referring now to FIG. 2, the hub 18 comprises a generally cylindrical main body portion 30 having a proximal end 32 and a distal end 34. A fitting 36 branches off from the main body portion 30. As will be explained in more detail below, the fitting 36 provides access to an auxiliary or secondary lumen of the sheath tubing 16. A pair of rings 38, 40 extend from the upper and lower edges of the main body portion 30 adjacent the distal end 34. The rings 38, 40 provide a means by which sutures can be attached to the hub 18 to secure the sheath assembly 12 to a surgical drape. A pair of mutually opposed locking slots 41a, b are formed or otherwise provided adjacent to the proximal end 32 of the hub 18. The function of the locking slots 41a, b is to cooperate with the locking tabs 29a, b on the luer 28 of the sheath assembly 12 to permit the luer 28 to lock to the hub 18.

Figure 3:
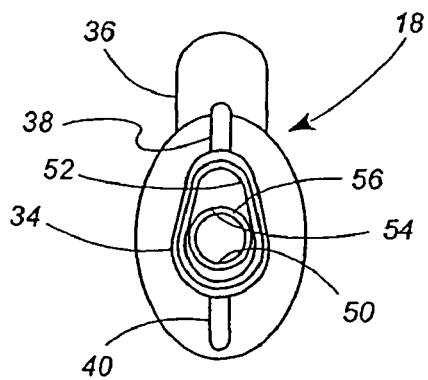
FIG. 3 is a front view of the hub of FIG. 2.
Figure 4:
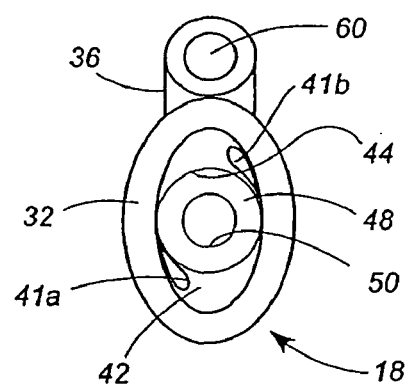
FIG. 4 is a rear view of the hub of FIG. 2.
Figure 5:
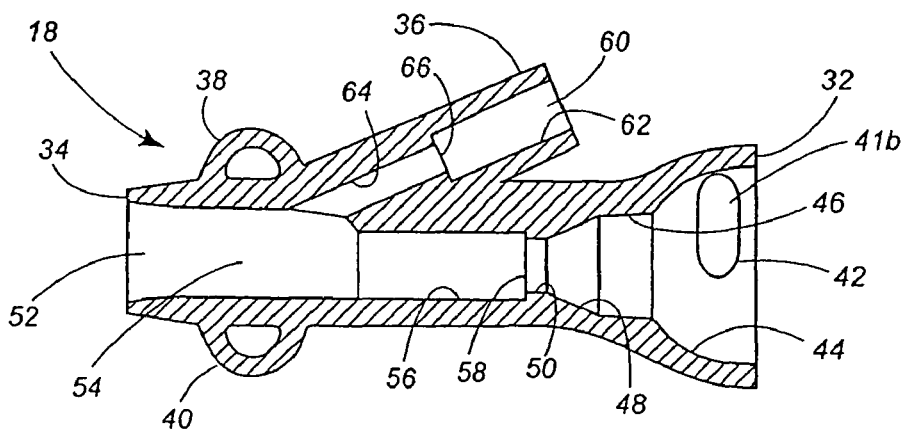
FIG. 5 is a side cutaway view of the hub of FIG. 2.
Figure 6:
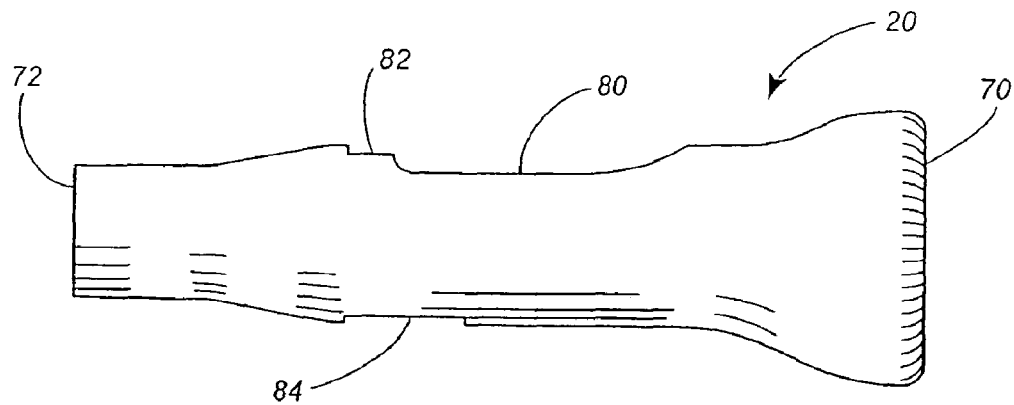
FIG. 6 is a side view of an elastomeric cover of the ureteral access sheath of FIG. 1.
Figure 7:
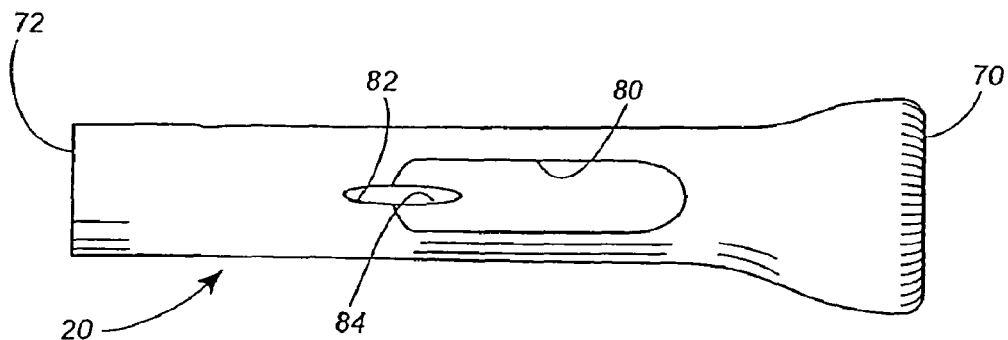
FIG. 7 is a top view of the elastomeric cover of FIG. 6.
Figure 8:
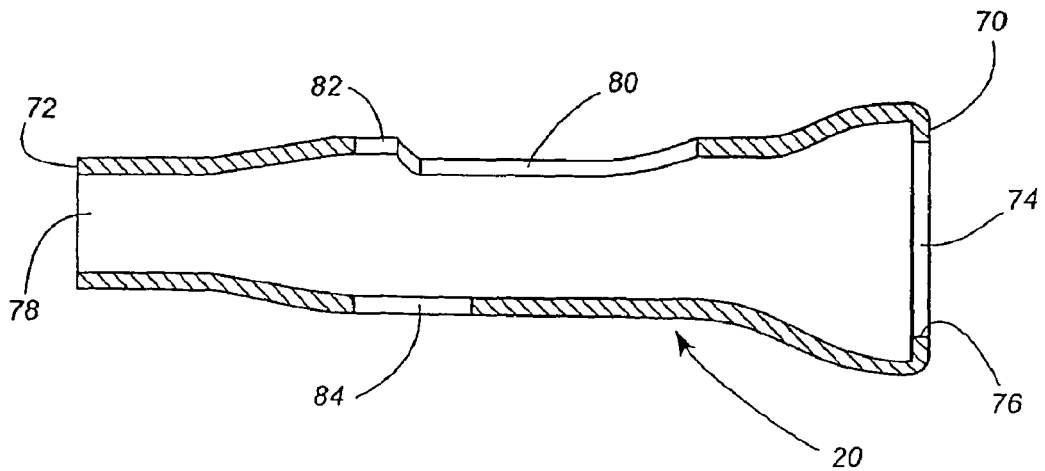
FIG. 8 is a side cutaway view of the elastomeric cover of FIG. 6.
Figure 9:
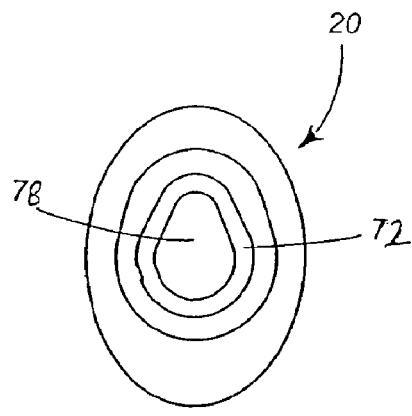
FIG. 9 is a front view of the elastomeric cover of FIG. 6.
Figure 10:
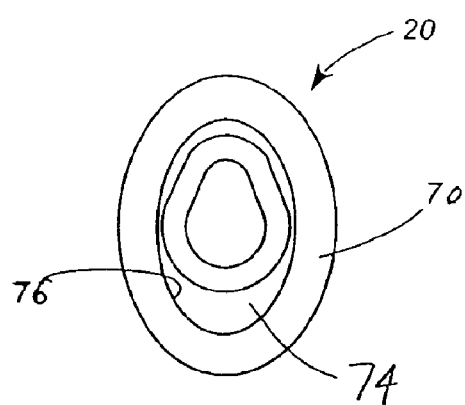
FIG. 10 is a rear view of the elastomeric cover of FIG. 6.
Figure 11:
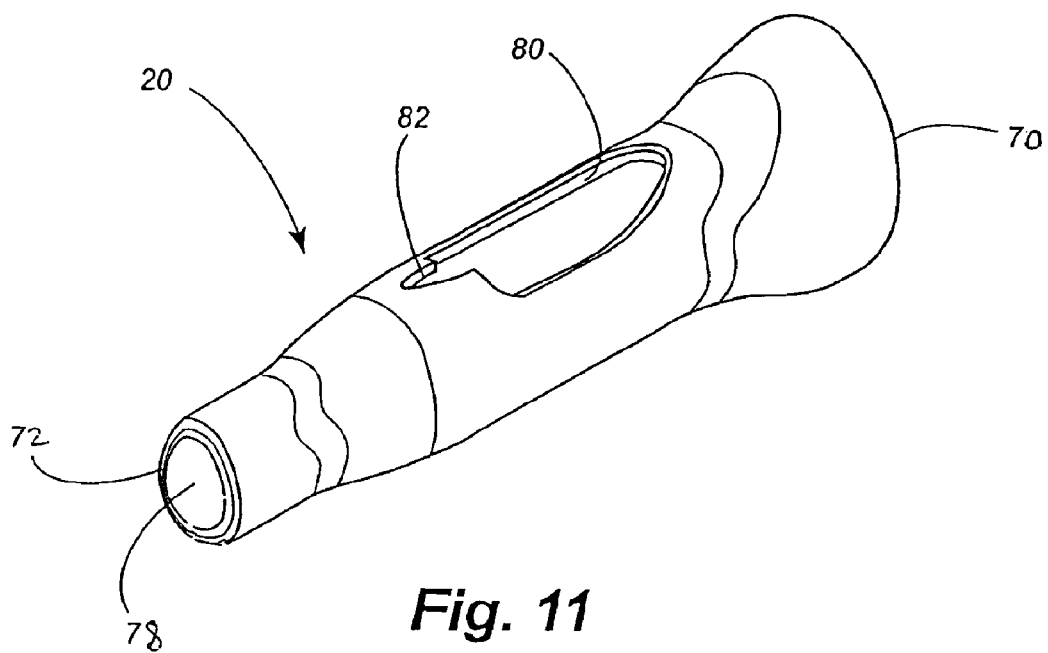
FIG. 11 is an isometric view of the elastomeric cover of FIG. 6.

The interior structure of the hub 18 is illustrated in FIGS. 3-5. An oblong opening 42 is formed in the proximal end 32 of the hub 18. Within the oblong opening 42, a bowl-shaped funnel portion 44 feeds into tapered section 46. The tapered section 46 in turn feeds into a second tapered section 48, which narrows into a short cylindrical bore 50. In the disclosed embodiment, the tapered section 46 is preferably configured to mate with the luer tip of a conventional Toomey syringe, for reasons that will be explained below.

At the distal end 34 of the hub 18, an ovate opening 52 is vertically elongated and is wider at its lower end than its upper end. An oblong front chamber 54 communicates with a cylindrical bore 56. The cylindrical bore 56 coaxially joins the smaller cylindrical portion 50. A step 58 is formed where the larger cylindrical bore 56 meets the smaller cylindrical portion 50.

Referring now to the fitting 36 at the upper end of the hub 18, an opening 60 is formed in the end of the fitting. Within the opening 60 is a cylindrical bore 62. The cylindrical bore 62 coaxially joins a smaller cylindrical bore 64, creating a step 66 where the bores 62, 64 join. The opposite end of the smaller cylindrical bore 64 opens into the chamber 54 in the distal end 34 of the hub 18.

Referring now to FIGS. 6-11, the elastomeric cover 20 has a proximal end 70 and a distal end 72. The proximal end 70 includes a vertically elongated opening 74 surrounded by an inwardly extending peripheral flange 76. The vertically elongated opening 74 corresponds in size and shape to the oblong opening 42 in the proximal end 32 of the hub 18. Similarly, a vertically elongated opening 78 in the distal end 72 of the elastomeric cover 20 generally corresponds in size and shape to the ovoid opening 52 in the distal end of the hub 18.

An elongated opening 80 is formed in the upper surface of the elastomeric cover 20. The opening 80 is rounded at its proximal and distal ends. The distal end of the opening 80 is in communication with a notch 82. A short elongated opening 84 is formed in the lower surface of the elastomeric cover 20.

FIGS. 12-14 illustrate the sheath tubing 16 of the sheath assembly 12. The sheath tubing 16 comprises a substantially circular tube 90 having a distal end 92 and a proximal end 94. The tube 90 defines a main lumen 96. In a preferred embodiment the main lumen 96 is substantially circular in cross-section. Unlike the lumens of multi-lumen catheters, the main lumen 96 is sized such that a relatively large surgical instrument, such as an endoscope or equivalently-sized instrument, can be passed through the lumen and the lumen used as a working channel. In one sense, this aspect of the tubing 16 defines the device as a sheath as opposed to a catheter. By way of example, the main lumen 96 ranges from about 4 French (Fr) to about 20 Fr in size. In one embodiment, the main lumen 96 ranges from about 10 Fr to about 12 Fr in size.

A U-shaped housing 98 sits atop the tube 90 and defines a secondary lumen 100 disposed above the main lumen 90. The secondary lumen 100 is typically smaller than the main lumen so as to facilitate insertion of the sheath tubing 16 into a relatively small vessel, such as a urethra. However, the secondary lumen 100 is large enough to receive relatively small devices, such as a guidewire or a laser fiber. The secondary lumen 100 has a cross-sectional area that is a fraction of that of the main lumen 96. By way of example, the secondary lumen 100 ranges from about 1 Fr to about 6 Fr in size. In one embodiment, the secondary lumen 100 ranges from about 2 to about 4 Fr in size. The housing 98 terminates at distal and proximal locations 102, 104 respectively, that are spaced inward from the ends of the tube 90. Thus the secondary lumen 100 terminates at locations which are axially displaced inward from the ends of the main lumen 96. The termination of the housing 98 forms an outlet of the secondary lumen 100. This outlet tapers in the direction of the distal end 92 of the tube 90 to facilitate insertion into and passage through a body vessel.

As illustrated in FIGS. 12-14, the disclosed embodiment comprises a tube 90 that is substantially circular in cross-section, a main lumen 96 that is substantially circular in cross-section, and a secondary lumen 100 that is substantially crescent-shaped in cross-section. However, it will be understood that the disclosed ureteral access sheath is not limited to these shapes, and that tubes, main lumens, and secondary lumens of other cross-sectional configurations may be employed as may be expeditious for particular surgical applications or convenient or for manufacturing purposes.

As is most clearly apparent from FIG. 14, the secondary lumen 100 is defined, at least in part, by opposed side walls 101. Those side walls 101 join the tube 90 of the US 2004/0267213 A1 main lumen 96 at joint portions 103, which comprise a relatively large amount of material. In addition to defining the secondary lumen 100, the side walls 101 and the joint portions 103 provide increased rigidity to the sheath tubing 16, which increases the kink resistance of the tubing. In particular, the additional material that forms the side walls 101 and the joint portions 103 increases the structural integrity of the sheath tubing 16 such that the tubing is less likely to kink when bent. The increased kink resistance is beneficial in that it results in improved patency when the sheath tubing is inserted into curved vessels, such as a ureter.

Testing has been performed to evaluate the kink resistance of the sheath tubing 16. In this testing, the sheath tubing 90 was coiled around various cylinders of different diameters. Once coiled around a given cylinder, the sheath tubing 16 was visually inspected to determine if any kinking occurred. If no kinking occurred, the test was considered a "pass." If kinking did occur, however, the test was considered a "fail."

During the testing, each of 15 sheath assemblies, each having a length of 35 centimeters (cm) and a 15 Fr circumferential measurement, passed after having been coiled around a cylinder having an outer diameter of one inch (in). Passing the kink test for a cylinder having such a small diameter indicates that the sheath tubing 16 is unlikely to kink during use, even when traversing a tortuous path within the body.

Assembly of the ureteral access sheath 10 will now be explained with reference to FIGS. 15-18. Referring first to FIG. 15, the proximal end 94 of the sheath tubing 16 is inserted through the opening 78 in the distal end 72 of the elastomeric cover 20 and all the way through the cover 20 until the proximal end of the sheath tubing 16 protrudes from the opening 74 in the proximal end 70 of the cover 20. The hub 18 is aligned with the sheath tubing 16 as shown in FIG. 15. Then, as depicted in FIG. 16, the hub 18 is advanced onto the sheath tubing 16. The proximal end 94 of the sheath tubing 16 enters the opening 52 at the distal end 34 of the hub 18. As the hub 18 is advanced further, the proximal end 94 of the tube 90 passes through the front chamber 54 of the hub 18 and enters the cylindrical bore 56. When the hub 18 has been fully advanced, the proximal end 94 of the tube 90 abuts the stop 58 at the rearward end of the cylindrical bore 56, as shown in FIG. 16.

Next, as illustrated in FIG. 17, the elastomeric cover 20 is drawn rearward over the hub 18. The distal end 34 of the hub 18 passes into the opening 74 in the proximal end 70 of the elastomeric cover 20. The elastomeric cover 20 is drawn rearward until the ring 38 on the upper surface of the hub resides within the notch 82 in the upper surface of the elastomeric cover 20, and the ring 40 on the lower surface of the hub resides within the short elongated opening 84 in the lower surface of the elastomeric cover. The fitting 36 extends through the elongated opening 80 in the upper surface of the elastomeric cover 20. When the hub 18 has been fully received into the elastomeric cover 20, the elastomeric cover snugly fits to the contours of the outer surface of the hub, as shown in FIG. 17.

Figure 18:
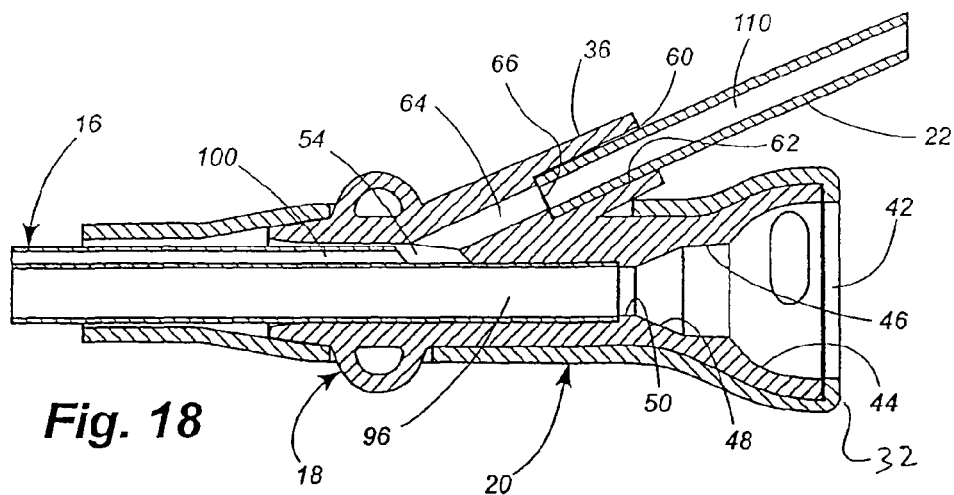
FIG. 18 is a side cutaway view of the assembly of FIG. 17 with a leader tube coupled to the hub of FIG. 2.

Referring now to FIG. 18, the leader tube 22 has been inserted into the hub 18. The end of the leader tube 22 is inserted into the opening 60 of the fitting 36 at the upper end of the hub 18. The end of the leader tube is advanced through the cylindrical bore 62 until it confronts the stop 66. The lumen 110 of the leader tube is in fluid communication with the secondary lumen 100 of the sheath tubing 16 by way of the smaller cylindrical bore 64 and the upper portion of the chamber 54 of the hub 18. The main lumen 96 of the sheath tubing 16 is in fluid communication with the opening 42 in the proximal end 32 of the hub 18 by way of the bore 50, second tapered section 48, tapered section 46, and funnel portion 44.

Figure 19:
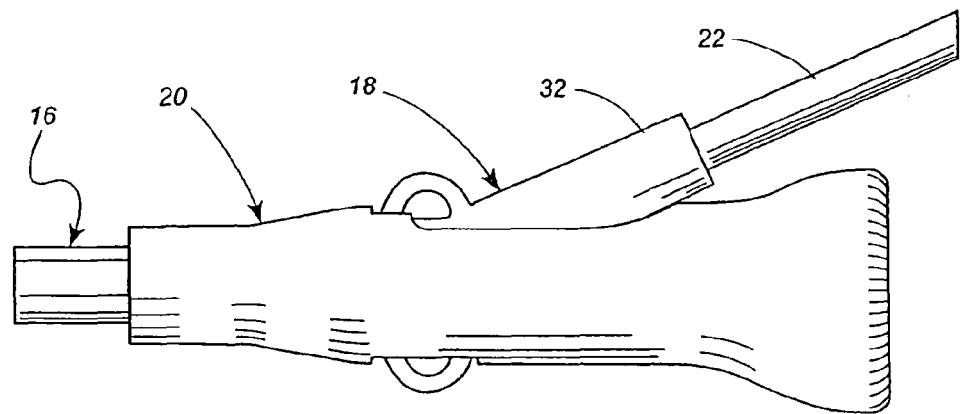
FIG. 19 is a side view of the assembly of FIG. 18.

FIG. 19 is a side view of the assembly of FIG. 18. The hub 18 is encased by the elastomeric cover 20. The leader tube 22 extends from the fitting 32 of the hub 18. The sheath tubing 16 extends from the distal end of the hub 18.

Figure 20:
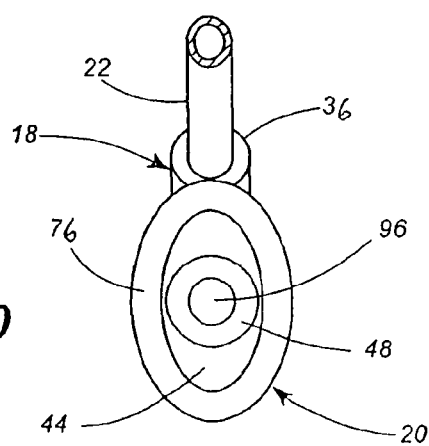
FIG. 20 is an end view of the assembly of FIG. 18.

FIG. 20 is a rear view of the assembly of FIG. 18. Once again, the hub 18 is encased by the elastomeric cover 20, and the leader tube 22 extends from the fitting 36 of the hub 18. The flange 76 of the elastomeric cover 20 conceals the rear edge (element 32 in FIG. 4) of the hub 18. The funnel portion 44 and the tapered portion 48 of the hub 18 are visible. The main lumen 96 of the sheath tubing is also visible.

Figure 21:
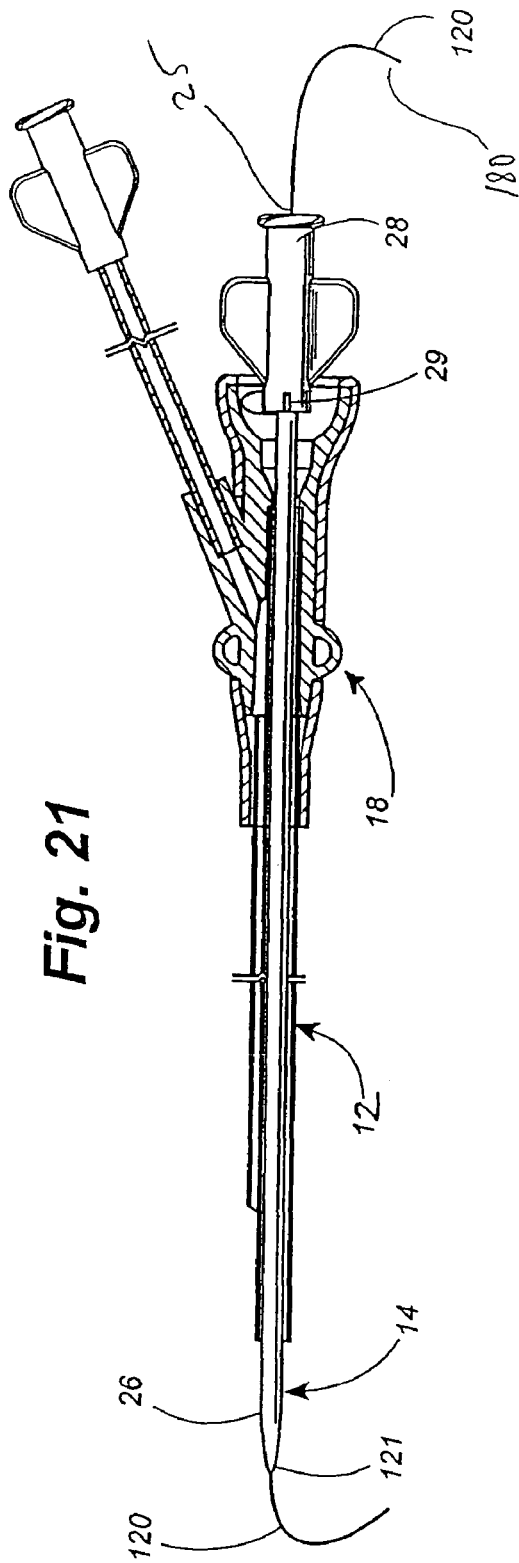
FIG. 21 is a side cutaway view of the ureteral access sheath of FIG. 1 with a guidewire extending through the main channel of the sheath.
Figure 22:
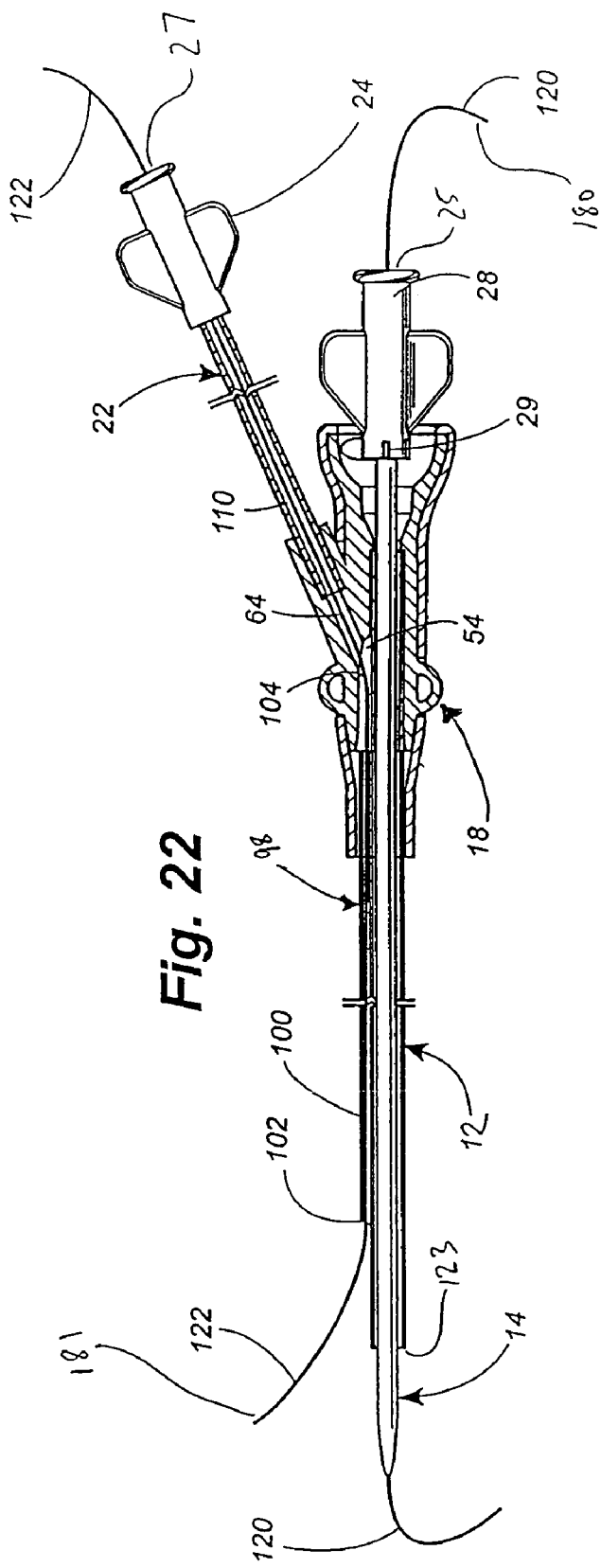
FIG. 22 is a side cutaway view of the ureteral access sheath of FIG. 21 with the first guidewire extending through the main channel of the sheath and a safety guidewire extending through the secondary channel of the sheath.
Figure 23:
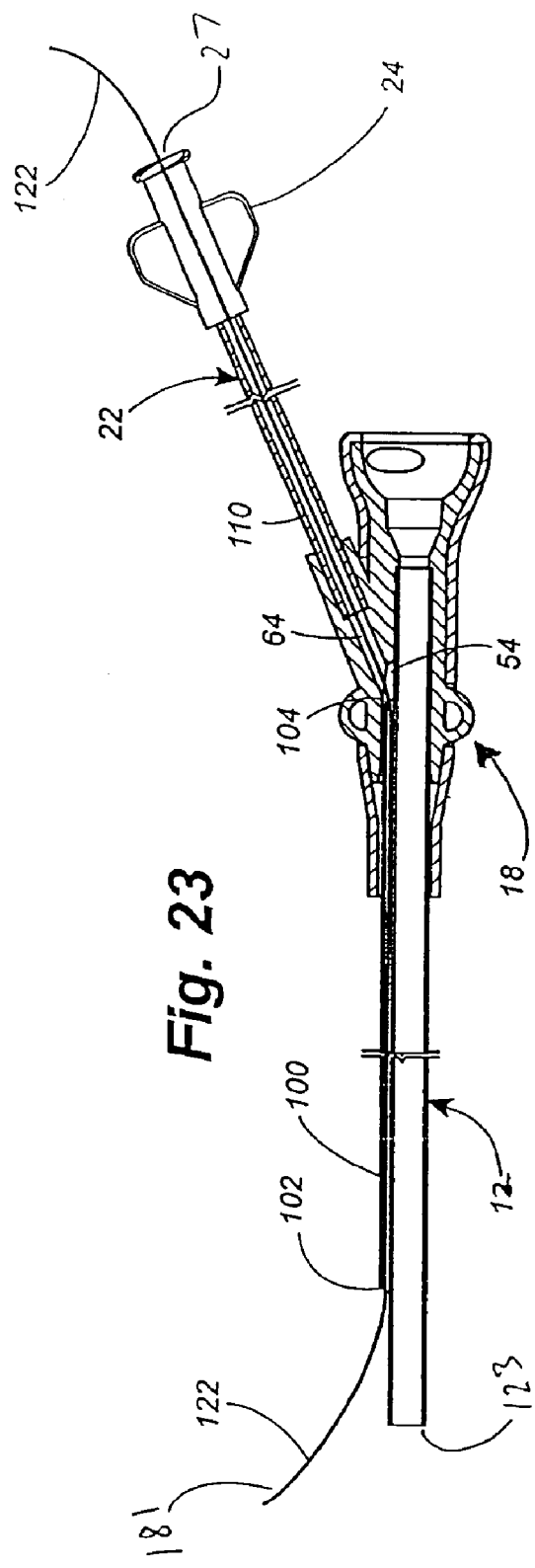
FIG. 23 is a side cutaway view of the ureteral access sheath of FIG. 22 with the first guidewire and dilator withdrawn from the main channel of the sheath and the safety guidewire remaining in place within the secondary channel of the sheath.

Use of the ureteral access sheath 10 to provide a working channel will now be explained with reference to FIGS. 21-23. Steps 1-4 are conventional and hence are not shown in the drawings.

1. A cystoscope is inserted into the patient's urethra and advanced into the bladder, where the ureteral orifices are identified.
2. Using the cystoscope, a guidewire 120 is inserted into the ureteral orifice.
3. Using fluoroscopy, the guidewire 120 is advanced through the ureter and into the kidney.
4. With the guidewire 120 carefully held in place, the cystoscope is removed over the guidewire.
5. Referring now to FIG. 21, the dilator assembly 14 is placed within the main lumen of the sheath assembly 12. The dilator assembly 14 is inserted into the sheath assembly 12 with the locking tab 29a of the dilator luer 28 oriented vertically. Then, when the dilator luer 28 is seated within the hub 18 of the sheath assembly 12, the dilator luer 28 is rotated 90° clockwise, and the locking tabs 29a, b on the dilator luer engage the locking slots 41a, b at the proximal end 32 of the hub 18 to lock the dilator assembly 14 to the sheath assembly 12.
6. With further reference to FIG. 21, the proximal end 180 of the guidewire 120 is inserted into the distal end 121 of the dilator tubing 26. The guidewire 120 is advanced through the dilator tubing 26 and exits through the proximal end 25 of the dilator luer 28.
7. The sheath assembly 12 with dilator assembly 14 in place is advanced over the guidewire 120 and into the ureter. Advancement and position of the ureteral access sheath is usually verified with fluoroscopy.
8. Referring now to FIG. 22, with the sheath assembly 12 in position with its distal end 123 within the ureter, the distal end 181 of a safety guidewire 122 is fed into the opening in the proximal end 27 of the luer fitting 24. The safety guidewire 122 is advanced through the lumen 110 of the leader tube 22 and into the small cylindrical bore 64, from where it enters the chamber 54 of the hub 18. The distal end 27 of the safety wire 122 then enters the secondary lumen 100 at the proximal end 104 of the housing 98 and traverses the length of the secondary lumen, exiting at the distal end 102 of the housing 98.
9. With the safety guidewire 122 thus positioned, the dilator assembly 14 and main guidewire 120 are removed from the sheath assembly 12, as shown in FIG. 23.

Figure 24:
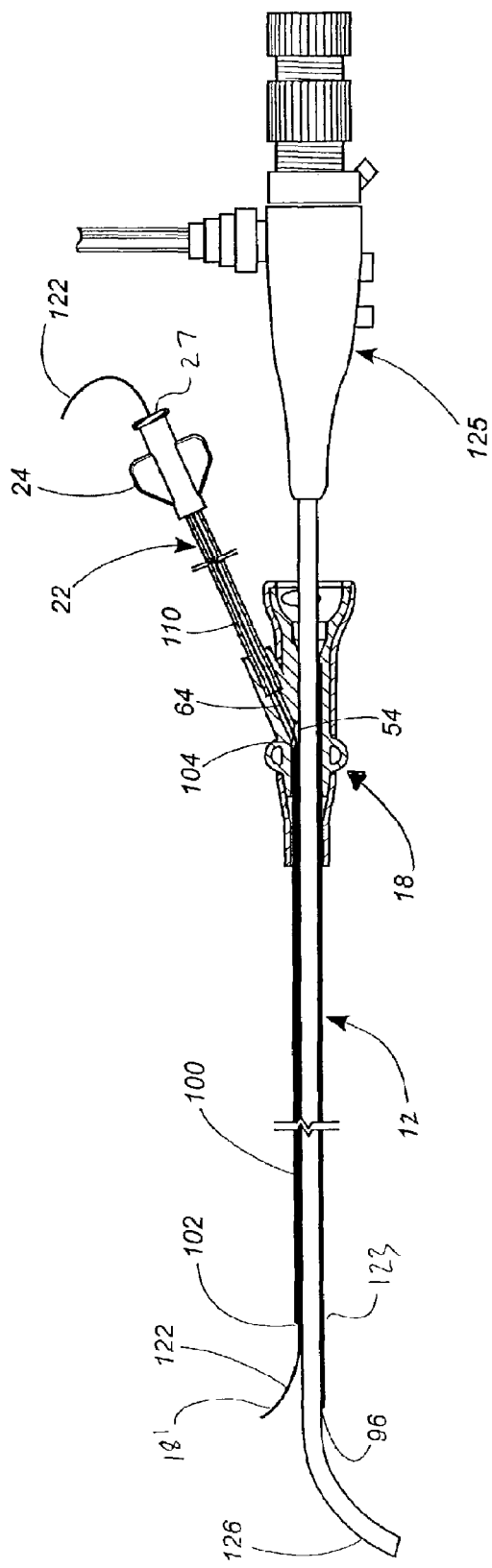
FIG. 24 is a side cutaway view of the ureteral access sheath of FIG. 23 with an endoscope sheath positioned within the main lumen of the ureteral access sheath.

Once the sheath assembly is in place to provide a working channel, a surgical procedure can commence. For example, a ureteroscope 125 has its distal end 126 introduced into the proximal end of the main lumen 96 of the sheath assembly 12, as shown in FIG. 24. The ureteroscope 125 is advanced through the sheath assembly 12 to the target site until the distal end 126 of the ureteroscope resides adjacent the target site. A surgical instrument, such as a grasper for crushing and removing calculi, is inserted through the working channel of the ureteroscope 125 and used in the conventional manner.

When it becomes necessary to irrigate the surgical field, an irrigation means is coupled to the female luer fitting 24 at the end of the leader tube 22, and an irrigation fluid is infused through the secondary lumen 100. The irrigation means can comprise, for example, a syringe, a bag of saline solution hung from an IV pole, an irrigation system including rollers for pressurized expulsion of saline solution from a bag, or the like. To facilitate coupling an irrigation means to the secondary lumen 100 while the safety guidewire 122 is still in place, a Y-fitting can be coupled to the female luer 24, the safety guidewire fed through one of the branches of the Y-fitting, and the irrigation means coupled to the other branch of the Y-fitting. Because the safety guidewire 122 occupies only a small portion of the cross section of the secondary lumen 100, irrigation can be effected through the same secondary lumen occupied by the guidewire.

Figure 25:
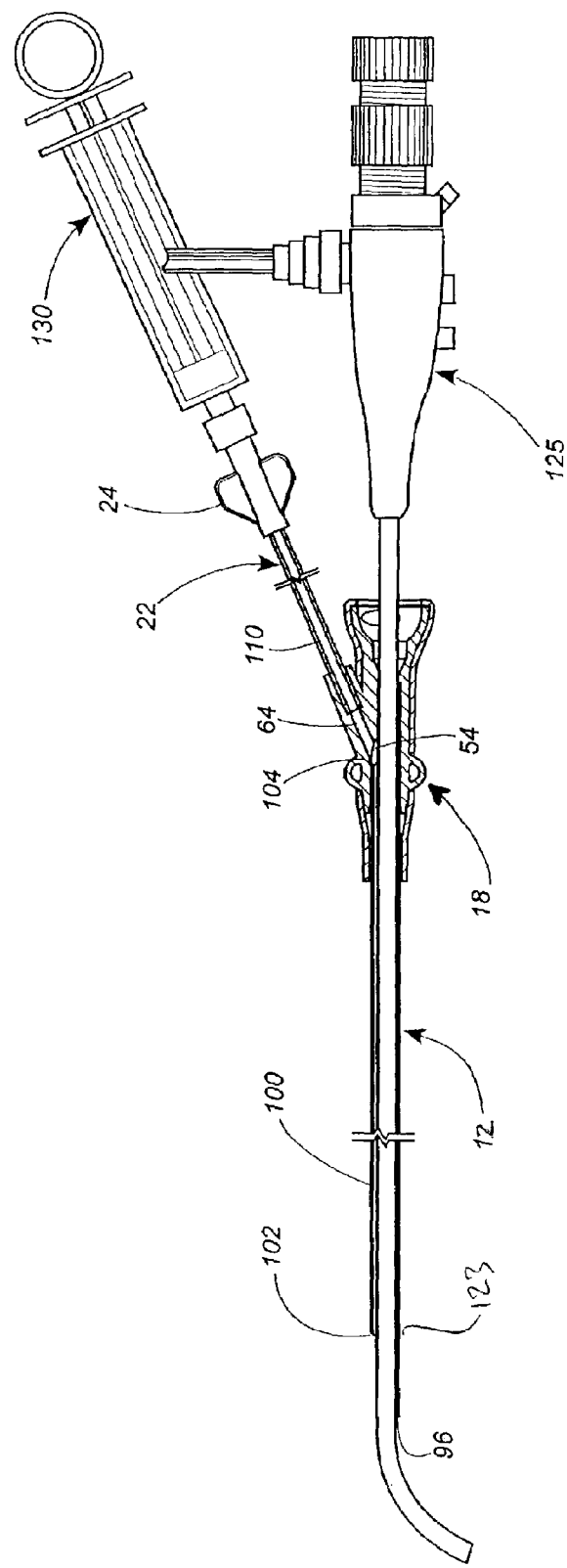
FIG. 25 is a side cutaway view of the ureteral access sheath of FIG. 1 with the dilator removed and with an endoscope sheath positioned within the main lumen of the ureteral access sheath and an irrigation syringe coupled to the secondary lumen of the sheath.

FIG. 25 shows an alternative configuration wherein the sheath assembly 12 is used to accommodate an endoscope 125 in the main working channel 96 and an irrigation means such as a syringe 130 is coupled to the secondary lumen 100. Even with the working channel of the ureteroscope 125 almost completely occupied by a surgical instrument, and even with the main working channel 96 of the sheath assembly 12 almost completely occupied by the ureteroscope 125, the surgical field can still be irrigated efficiently by infusing the irrigation fluid through the secondary lumen 100.

Figure 26:
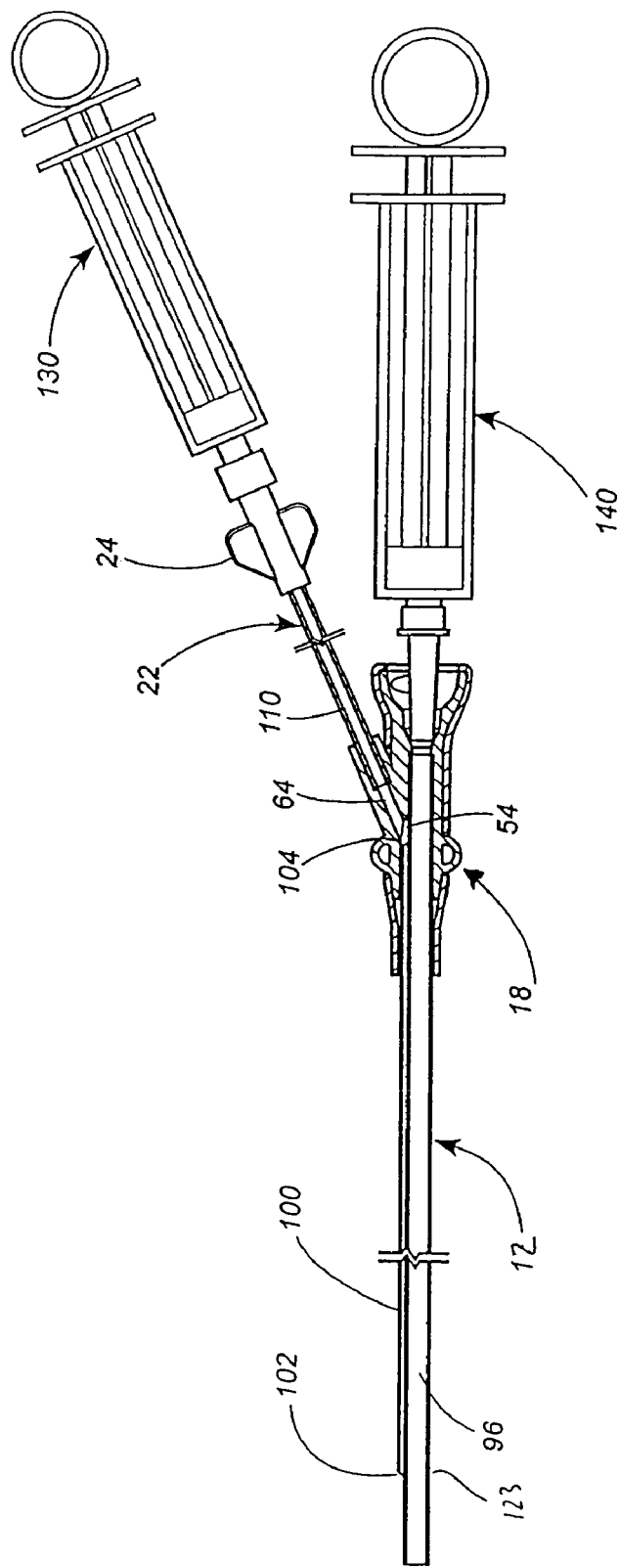
FIG. 26 is a side cutaway view of the ureteral access sheath of FIG. 1 with the dilator removed and with an aspiration syringe coupled to the main lumen of the ureteral access sheath and an irrigation syringe coupled to the secondary lumen of the sheath.

FIG. 26 shows yet another alternative configuration wherein the sheath assembly 12 is used to accommodate an aspiration means such as a Toomey syringe 140 coupled to the main working channel 96, and an irrigation means such as a syringe 130 coupled to the secondary lumen 100. With this configuration, simultaneous irrigation and aspiration can be accomplished, which can create a turbulent effect in the operative field that is useful for removing particles and debris.

The ureteral access sheath 12 of the disclosed embodiment thus provides a number of advantages over known prior art ureteral access sheaths. Because of the dual lumens 96, 100, the sheath assembly 12 can be configured as follows:

Device-Device. Both lumens can be occupied by medical devices. While the main working channel will most often be occupied by a ureteroscope, the secondary channel can be occupied by a safety guidewire, a laser fiber, a stone basket, a grasper, or any other medical device suitable to the procedure being performed. In the case of placing a safety guidewire in the secondary lumen, the sheath assembly 12 can be rapidly repositioned without the need for multiple backloads.

Device-Irrigation. The main working channel can be occupied by a ureteroscope, and the secondary working channel can be coupled to a source of irrigation such as a syringe, irrigation bag, irrigation system, or the like. Thus even when the main working channel of the ureteroscope is almost completely occupied by a surgical instrument, the surgical field can be irrigated efficiently by infusing the irrigation fluid through the secondary lumen.

Device-Device/Irrigation. The main working channel can be occupied by an instrument such as a ureteroscope 125. A Y-fitting can be attached to the female luer 24 of the leader tube 22. The safety guidewire 122 can be fed through the opening in one branch of the Y-fitting, and an irrigation means can be coupled to the other branch of the Y-fitting so that irrigation can be achieved while the safety guidewire is still in place within the secondary lumen 100.

Irrigation-Irrigation. The main working channel can be coupled to an aspiration means such as a Toomey syringe by locking the luer of the syringe into the tapered section 46 of the hub 18, and the secondary channel can be coupled to a source of irrigation such as a syringe, irrigation bag, irrigation system, or the like. Thus it is possible to irrigate the operative field through the secondary channel while aspirating the field through the main channel, setting up a turbulent flow in the operative field which is helpful in removing particles and debris.

FIG. 27 illustrates an alternative embodiment of a sheath tubing 16'. The sheath tubing 16' includes a first U-shaped housing 98A on top of the tube 90 and a second U-shaped housing 98B on the side of the tube opposite the first housing 98A. Two secondary lumens 10A, 100B are thus formed on opposite sides of the main lumen 96. As can be appreciated from FIG. 27, the existence of two secondary lumens 100A, 100B results in increased kink resistance due to the additional material provided by the opposed side walls 101 and joint portions 103 of the secondary lumens (see discussion of FIG. 14 above).

FIG. 28 illustrates an alternative embodiment of a hub 18' for use with the sheath tubing 16' of FIG. 27. The hub 18' differs from the hub 18 previously described in that it has two fittings 32A, 32B. In addition, the opening 52' at the forward end of the hub 18' is reconfigured to accommodate the sheath tubing 16' with two U-shaped housings 98A, 98B.

FIG. 29 depicts an alternative embodiment of a sheath assembly 12' that comprises a sheath tubing 16', a hub 18', and two leader tubes 22A, 22B. Each of the two leader tubes 22A, 22B is in fluid communication with a separate one of the two secondary lumens 10A, 100B. In the case of the sheath tubing 16' having two secondary lumens 100A, 100B, the irrigation fluid is introduced through a secondary lumen different from the secondary lumen occupied by the guidewire. Or, a guidewire can occupy one channel while a grasper, laser fiber, or stone basket is used in the other secondary channel. As yet another option, a surgical instrument such as a grasper, stone basket, laser fiber, or the like can be used in one secondary channel while the other secondary channel is being used for irrigation. As still another option, one secondary channel can be hooked up to an irrigation means while the other secondary channel is hooked up to an aspiration means. In this manner simultaneous irrigation and aspiration to create a turbulent wash in the surgical field can be performed without removing a surgical instrument such as a ureteroscope from the main working channel.

Figure 30:
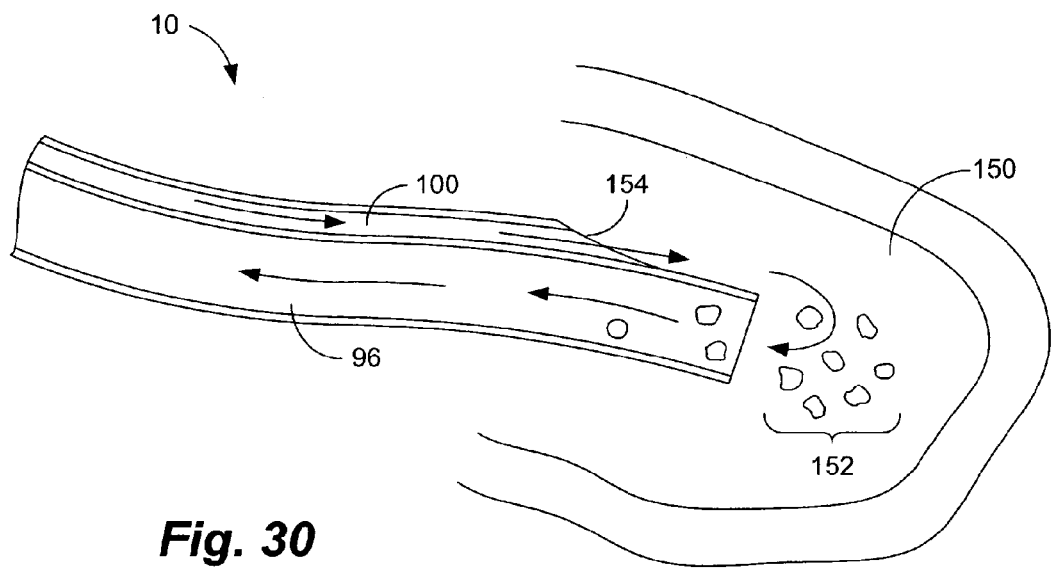
FIG. 30 is a schematic view depicting flushing of particulate material from a body cavity using a ureteral access sheath.

FIG. 30 depicts flushing of material, in this case kidney stone fragments, from a body cavity using the ureteral access sheath 10. As described above in relation to FIG. 26, the secondary lumen 100 can be used during surgical procedures to irrigate an area within the body, such as a kidney, and the main lumen 96 can be used to aspirate such an area, either simultaneously or in an alternating fashion. Because of the relatively large size of the main lumen 96, relatively large debris can be removed from a body cavity or vessel. Therefore, when the sheath 10 is inserted into a body cavity 150, such as the interior of a kidney, that contains particulate material 152, such as stone fragments, irrigation liquid can be ejected from an outlet 154 of the secondary lumen 100 to facilitate removal of the fragmentary material from the cavity via the main lumen 96.

As is depicted by directional arrows in FIG. 30, the irrigation liquid can flow through the secondary lumen 100, out from its outlet 154, and into the cavity 150 to create a turbulent flow. If the pressure within the main lumen 96 is less than that within the cavity 150, for example if a suction is created using a syringe or other aspiration mechanism, the liquid will flow into the main lumen 96, taking the particulate material 152 along with it. In such a case, the particulate material 152 can be drawn out from the cavity 152 through the main lumen 96. Although particulate (e.g., stone fragment) removal is illustrated in FIG. 30, other materials can be removed in similar manner. For instance, material that obscures viewing within a cavity or vessel, such as blood or mucus, can be removed via the main lumen 96, irrespective of whether irrigation is provided with the secondary lumen 100.

Figure 31:
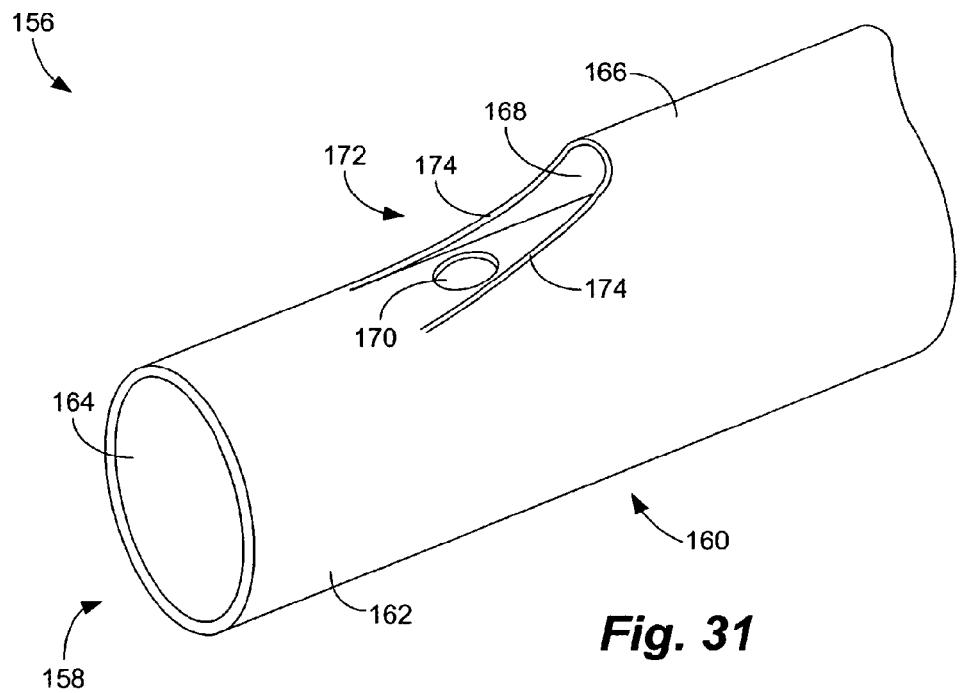
FIG. 31 is a partial perspective view of a distal end of tubing of a further alternative ureteral access sheath.
Figure 32:
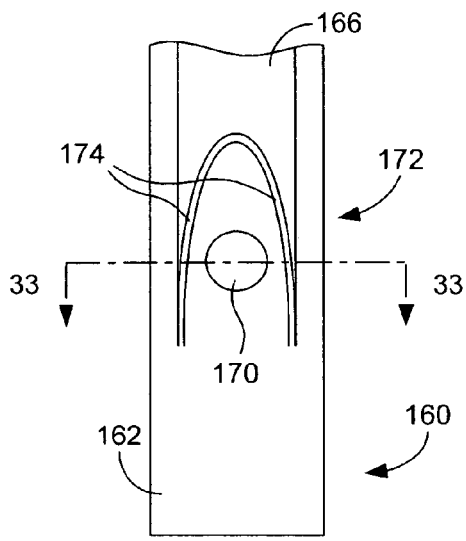
FIG. 32 is a partial top view of the distal end of the sheath tubing shown in FIG. 31.
Figure 33:
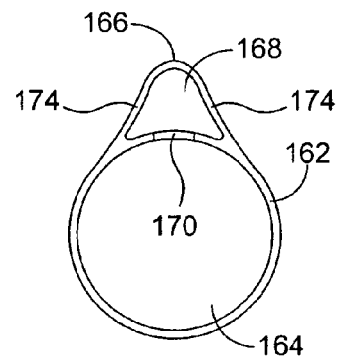
FIG. 33 is a cross-sectional view of the sheath tubing shown in FIG. 32 taken along line 33-33.

FIGS. 31-34 illustrate a further alternative embodiment of a ureteral access sheath 156. As is apparent from FIG. 31, which illustrates a distal end 158 of the sheath 156, the sheath tubing 160 has a configuration that is similar to that of the sheath tubing 16 shown in FIGS. 1-26. Accordingly, the sheath tubing 160 includes a substantially cylindrical tube 162 that defines a main lumen 164, and a U-shaped housing 166 that defines a secondary lumen 168. Unlike the sheath tubing 16, however, the sheath tubing 160 includes an opening 170 that extends through the tube 162 to provide access to the main lumen 164 from the exterior of the tube. The opening 170 can be located adjacent or within the bounds of the lumen outlet 172. For instance, in the embodiment shown in FIG. 31, the opening 170 can be positioned within an area defined by opposed side walls 174 of the U-shaped housing 166 so as to shield the opening. As is shown in FIG. 31, the side walls 174 taper toward the distal end 158 of the sheath tubing 160 to facilitate insertion into and passage through a body vessel.

Due to the provision of the opening 170, damage to patient tissue can be avoided in cases in which the flow of irrigation fluid from the secondary lumen 164 is obstructed by that tissue. In such a situation, irrigation fluid, instead of being blocked, may pass out from the lumen outlet 172, in through the opening 170, and into the mail lumen 164. Such a situation is illustrated in FIG. 34.

Figure 34:
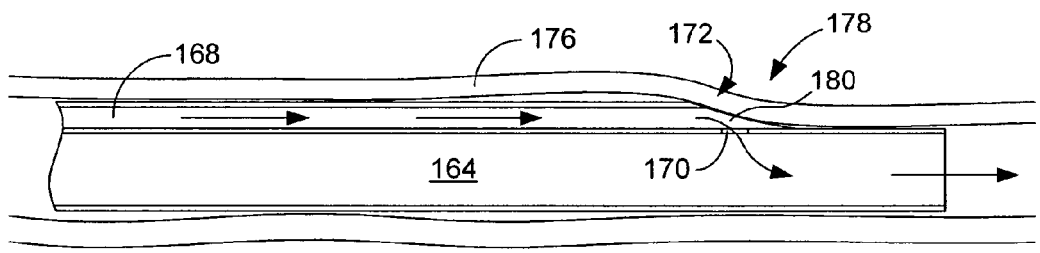
FIG. 34 is a schematic view depicting irrigation of a body vessel using the ureteral access sheath shown in FIGS. 31-33.

As is shown in FIG. 34, when the sheath tubing 160 is passed through a patient vessel 176 and a constriction 178 is encountered that closes off flow from the outlet 172 into the vessel, irrigation fluid (indicated by direction arrows) can still pass through the opening 170 and into the main lumen 164 so that vessel is not overpressurized. This flow is possible due to the opposed side walls 174. In particular, the side walls 174 shield the opening 170 by maintaining a gap 180 between the vessel walls and the opening to keep the opening accessible from the lumen outlet 172. Because the opening 170 provides a path for the irrigation liquid to traverse, the opening serves as a pressure relief mechanism that can avoid damage to the vessel 176.

Figure 35:
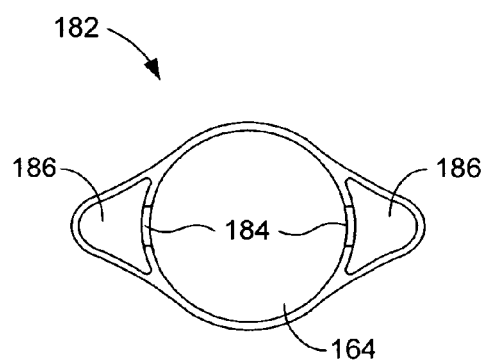
FIG. 35 is a cross-sectional view of a further alternative sheath tubing.

FIG. 35 illustrates a variant on the embodiment shown in FIGS. 31-34. Specifically, FIG. 35 illustrates sheath assembly tubing 182 in which two openings 184 are provided, one opening being provided for each of two separate secondary lumens 186. With this configuration, flow through both of the secondary lumens 186 can continue even if the outlets of both lumens are obstructed.

Figure 36:
FIG. 36 is a partial view of a distal end of an alternative dilator that may be used with a sheath assembly.

FIG. 36 illustrates an alternative dilator 188 that can be used in conjunction with any of the sheath assemblies described in this disclosure. The dilator 188 includes a shaft 190 and a relatively soft tip 192 that extends from the shaft. The relatively soft tip 192 is constructed of a resilient polymeric material, such as a polyurethane material and, for example, has a Durometer hardness that ranges from about 50 A to about 65 D. In some embodiments, the tip 192 has a Durometer hardness that ranges from about 90 A to about 55 D. When the material used to construct the tip 192 is within those ranges, the tip can be formed so as to be very pliable. This pliability reduces the likelihood of damaging patient tissue during insertion of the dilator 188 because the dilator tip 192 can deflect or yield when contact is made with patient tissue.

Figure 37:
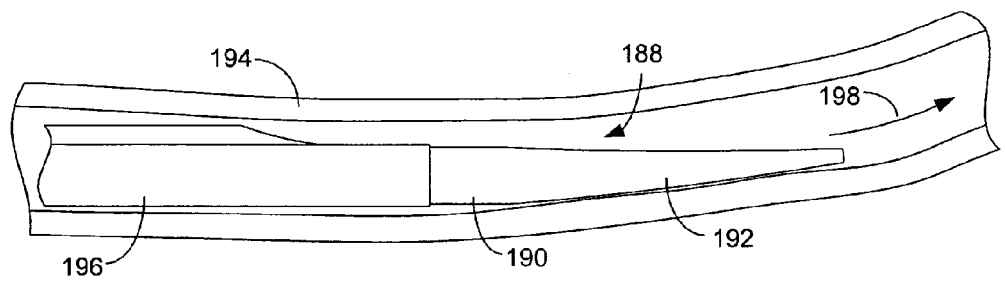
FIG. 37 is a schematic view depicting traversal of the dilator of FIG. 36 and sheath tubing through a body vessel.

The pliability of the relatively soft tip 192 is illustrated in FIG. 37. As is depicted in that figure, when the dilator 188 is inserted through a patient vessel 194 along with sheath tubing 196 (in the direction of arrow 198), the tip 192 bends to, at least to some degree, conform to the contour of the interior vessel walls so that the vessel is not damaged (e.g., lacerated).

Figure 38:
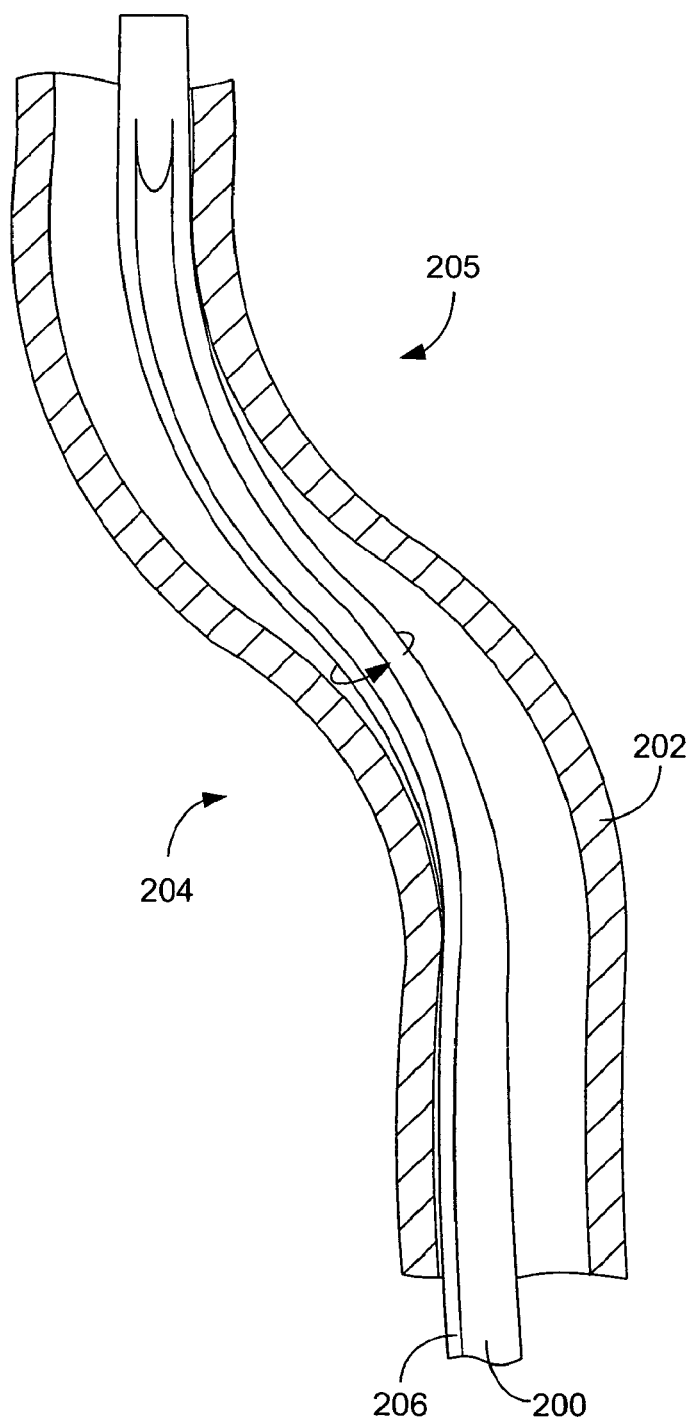
FIG. 38 is a schematic view depicting self-alignment of sheath tubing within a body vessel.

Due to the relative rigidity obtained by the presence of the one or more secondary lumens, the ureteral access sheaths described in the foregoing can self-align when inserted through a patient vessel. An example of this phenomenon is illustrated in FIG. 38. As is shown in that figure, the sheath tubing 200 of an access sheath has been inserted into a body vessel 202, such as a ureter. The vessel includes bends 204 and 205, so as to define a serpentine path. Assuming an insertion direction through the vessel 202 from bottom to top in the orientation of FIG. 38, the U-shaped housing 206 that forms the secondary lumen begins on the left side of the sheath tubing 200, prior to the bends 204 and 205. As the vessel 202 is traversed upward, however, the sheath tubing 200 twists through 90 degrees about its longitudinal axis (as indicated by a curved arrow) so that, after the bends 204 and 205, the U-shaped housing 206 is positioned in the center or top of the sheath tubing.

This phenomenon occurs, at least in part, due to the relative stiffness of the side of the sheath tubing 200 that comprises the U-shaped housing 206. As described above in relation to FIG. 14, the additional material associated with the walls of the secondary lumen and the joint areas at which those walls join the tube of the main lumen increase the rigidity of the sheath along the side of the sheath that includes the secondary lumen. Because that side is stiffer than the remainder of the tubing, the side of the sheath that comprises the U-shaped housing 206 automatically migrates toward the straightest path along the vessel, away from the bends. In other words, the U-shaped housing 206 naturally twists away from the walls that define such bends (on the left and right sides of vessel interior in the example of FIG. 38). Notably, such migration can occur in various directions. For instance, in the example shown in FIG. 38, the sheath tubing 200 could have, alternatively, twisted such that the U-shaped housing 206 is positioned on the "bottom" of the tubing (i.e., 90 degrees in the opposite direction traveled in FIG. 38) given that that position is also away from the walls that define the walls of the vessel that define the bends.

Because of this self-aligning action, the sheath tubing 200 automatically aligns itself within the body vessel in an orientation in which greater patency can be achieved. Specifically, the tubing 200 is aligned within the vessel so as to be more likely to remain open when a serpentine path is traversed. This phenomenon can be observed when multiple bends of a vessel are traversed.

As noted above, the presence of at least one secondary lumen increases the structural integrity of the sheath tubing of the ureteral access sheath and reduces kinking of the sheath during surgical procedures. Further kink resistance is provided when a guidewire, such as a safety wire, is inserted inside the secondary lumen in the manner indicated in FIGS. 39 and 40. As indicated in FIG. 39, sheath tubing 208 is illustrated in partial, cutaway view. As the other sheath tubings described in the foregoing, the tubing 208 comprises a main lumen 210 defined by a substantially cylindrical tube 212, and a secondary lumen 214 defined by a U-shaped housing 216. Disposed within the secondary lumen 214 is a guidewire 218, which extends along the entirety of the secondary lumen 214. By way of example, the guidewire comprises a coiled steel guidewire or a nitinol guidewire.

The presence of the guidewire 218 within the secondary lumen 214 provides additional strength to the sheath tubing 208 beyond that provided by the opposed walls 220 and the joint portions 222 (FIG. 40) of the U-shaped housing to resist kinking. In some cases, provision of the guidewire 218 within the secondary lumen 214 completely prevents kinking by not permitting the secondary lumen to collapse. Without collapsing of the secondary lumen 214, the sheath tubing 208 as a whole is unlikely to kink during a surgical procedure. Therefore, kinking can be prevented during surgical procedures by inserting a guidewire into the secondary lumen 214 prior to performing a surgical procedure. Similar results can be achieved if a guidewire is used in multiple lumens of the sheath tubing 208 (not shown).

Finally, it will be understood that the preferred embodiment has been disclosed by way of example, and that other modifications may occur to those skilled in the art without departing from the scope and spirit of the appended claims.

What is claimed is:

1. A sheath assembly designed for insertion into a ureter of a body, comprising:
   a sheath tubing having:
      a main lumen having a first cross-sectional area, a first length, and a distal end outlet;
      a secondary lumen having a second cross-sectional area less than the first cross-sectional area, a second length less than the first length, and a distal end outlet terminating proximal of the main lumen distal end outlet; and
      an opening adjacent the secondary lumen distal end outlet extending through a wall circumscribing the main lumen to provide access to the main lumen; and
   a dilator assembly including a dilator tubing having a pliable tip.

2. The sheath assembly according to claim 1, wherein the pliable tip has a Durometer hardness that ranges from about 50 A to about 65 D.

3. The sheath assembly according to claim 1, wherein the pliable tip has a Durometer hardness that ranges from about 90 A to about 55 D.

4. The sheath assembly according to claim 1, wherein the main lumen ranges from about 4 French to about 20 French in size.

5. The sheath assembly according to claim 1, wherein the main lumen ranges from about 10 French to about 12 French in size.

6. The sheath assembly according to claim 1, wherein the secondary lumen ranges from about 1 French to about 6 French in size.

7. The sheath assembly according to claim 1, wherein the secondary lumen ranges from about 2 French to about 4 French in size.

8. The sheath assembly according to claim 1, wherein the secondary lumen comprises opposed side walls that connect with the main lumen to form joint portions, the opposed side walls and the joint portions increasing a structural integrity of the sheath tubing to reduce kinking.

9. The sheath assembly according to claim 8, wherein the opposed side walls of the secondary lumen comprise a tapered portion at the distal end outlet thereof.

10. The sheath assembly according to claim 9, wherein the opening is positioned between the tapered portion of the opposed side walls.

11. The sheath assembly according to claim 1, further comprising a hub that is coupled to a proximal end of the sheath tubing.

12. The sheath assembly according to claim 11, further comprising an elastomeric cover that at least partially encases the hub.

13. The sheath assembly according to claim 11, wherein the hub comprises first and second locking slots, and wherein the dilator assembly comprises first and second locking tabs configured to cooperate with the first and second locking slots to lock the dilator assembly to the hub.

\* \* \* \* \*